United States Patent [19]

Carpenter

[11] 4,252,120
[45] Feb. 24, 1981

[54] COLOSTOMY SEAL

[75] Inventor: Steven Carpenter, Chichester, England

[73] Assignee: Matburn (Holdings) Ltd., London, England

[21] Appl. No.: 21,589

[22] Filed: Mar. 19, 1979

[30] Foreign Application Priority Data

Mar. 23, 1978 [GB] United Kingdom ............... 11658/78

[51] Int. Cl.³ .............................................. A61F 5/44
[52] U.S. Cl. .................................................. 128/283
[58] Field of Search ........................... 128/283; 428/43

[56] References Cited

U.S. PATENT DOCUMENTS

| 2,341,984 | 2/1944 | Graves | 128/283 |
| 3,302,647 | 2/1967 | Marsan | 128/283 |
| 4,095,599 | 1/1978 | Simonet-Halbe | 128/283 |

FOREIGN PATENT DOCUMENTS 850153 7/1977 Belgium .
1050070 12/1966 United Kingdom .
1521796 8/1978 United Kingdom .

OTHER PUBLICATIONS

"Karaya Gum Washers", *The Perma-Type Co., Inc.* Trade Bulletin 2-1971.

Primary Examiner—Robert W. Michell
Assistant Examiner—Thomas Wallen
Attorney, Agent, or Firm—McAulay, Fields, Fisher, Goldstein & Nissen

[57] ABSTRACT

A device for sealing an ostomy bag to the skin of a patient, comprises a sheet of material capable of adhering to the skin of a patient so as to provide a substantially liquid tight seal. The sheet has a slit or cut extending as a spiral or the like. An aperture may then be produced in the sheet as desired by unwinding the coil defined by the spiral slit or cut. The sheet may be of a gelatinous material having a basis of Karaya gum and/or another hydrophilic material.

7 Claims, 5 Drawing Figures

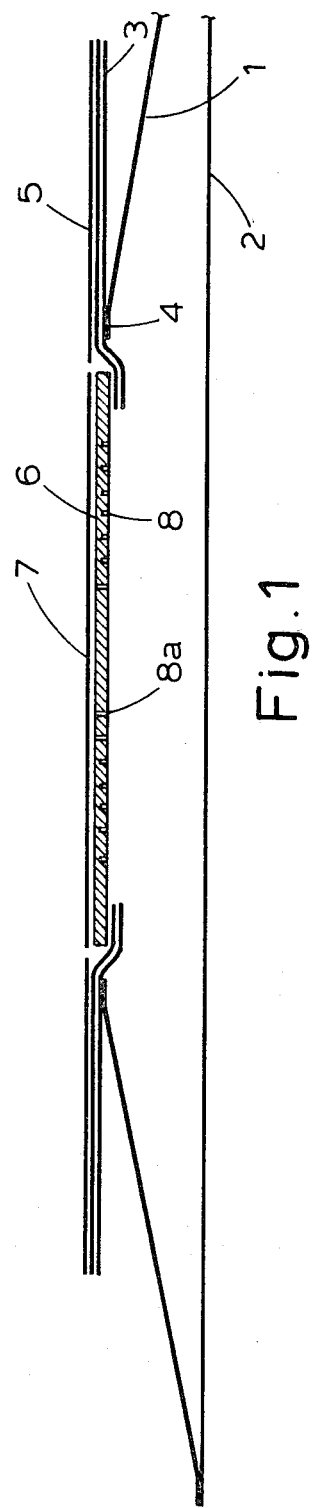
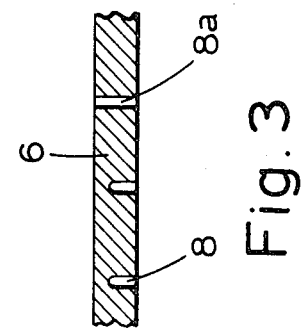
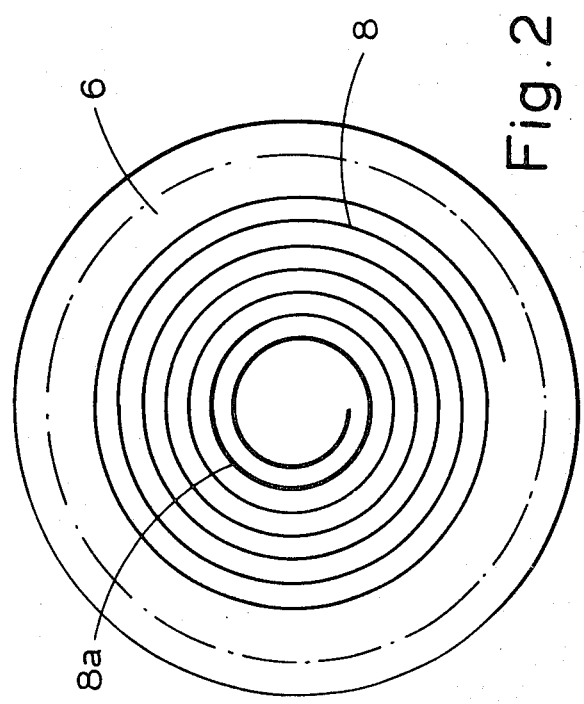

COLOSTOMY SEAL

BACKGROUND OF THE INVENTION

It is well known that some abdominal surgery may result in the formation of a faecal or urinary stoma and that the contents of the intestine or bladder will flow from the stoma outside the control of the patient. This will also be the case when a fistula develops between an internal organ and the abdominal surface or when an abdominal (or other) wound site breaks down allowing leakage of fluid from within the cavity. In all such cases it will be necessary to provide the patient with a means of collecting the waste material; this usually takes the form of a pouch or bag which is commonly called an "ostomy" bag.

The material to be collected is often corrosive to the skin of the patient and protection must be provided to prevent leakage around the stoma. In order to protect this area of skin, it is commonplace for the patient to apply to the skin a suitable covering which is often a gelatinous ring of a material the base of which is Karaya gum. These rings are sometimes separate items over which the collection bags also fit, or, sometimes, the rings are actually incorporated as part of the construction of a collection bag. There are considerable variations in the size of the stoma from patient to patient and it is therefore necessary for manufacturers of ostomy products to provide a significant range of protective rings of varying diameters. An object of the present invention is to provide a way of avoiding the need to supply such a range of rings, and provide a wider ringe of variations to the size of the aperture of the ring.

BRIEF SUMMARY OF THE INVENTION

Accordingly, the invention provides a device for sealing an ostomy bag to the skin of a patient, the said device comprising a sheet of material capable of adhering to the skin of a patient so as to provide a substantially liquid tight seal, wherein the said sheet has a slit or cut extending as a spiral or the like whereby an aperture can be produced in the sheet as desired by unwinding the coil defined by the spiral slit or cut. The depth of cut depends on the nature of the material of the sheet and may penetrate only partially through the thickness of the sheet although it preferably pentrates completely through the sheet at the centre of the coil.

The sheet is preferably a disc and the slit or cut preferably formed by stamping the sheet and extends about two thirds or to three quarters of the thickness of the sheet. With this arrangement the patient can push out the centre of the coil defined by the spiral cut or slit and then unwind it from the inside of the coil until the hole is of the correct size to fit the stoma of the patient. Preferably, the sheet is formed of a material of which the basis is Karaya gum and/or another hydrophilic material having similar physical and skin care properties and available in sheet form. The sheet is preferably gelatinous and of a reasonable degree of rigidity. The material must be sufficiently pliable to enable the coil to be unwound. If desired, the sheet may comprise two or more layers. For example, it may comprise a support layer of plastics foam or plastics sheet material and a layer of Karaya gum base material.

The invention also provides an ostomy bag having a back wall which can be placed in contact with the skin of a patient, the said back wall having a hole in which the stoma of the patient may be received, a flexible ring one surface of which is secured to the back surface of the back wall of the bag and which surrounds the opening in the bag and the other surface of which is adhesive so that it can be secured to the skin of the patient, the hole in the back wall of the bag being closed by a sheet of material capable of adhering to the skin of the patient to provide a substantially liquid tight seal, the said sheet being provided with a slit or cut extending as a spiral or the like and the said sheet being secured to the flexible ring. Preferably, the sheet is secured to the flexible ring in such a way that its back surface is flush or approximately flush with the back surface of the bag.

BRIEF DESCRIPTION OF THE DRAWINGS

FIG. 1 is a sectional view of part of an ostomy bag,
FIG. 2 illustrates a sealing device for the bag,
FIG. 3 is a detail view of part of the sealing device of FIGS. 1 and 2.

DESCRIPTION OF PREFERRED EMBODIMENTS

Figure 4:
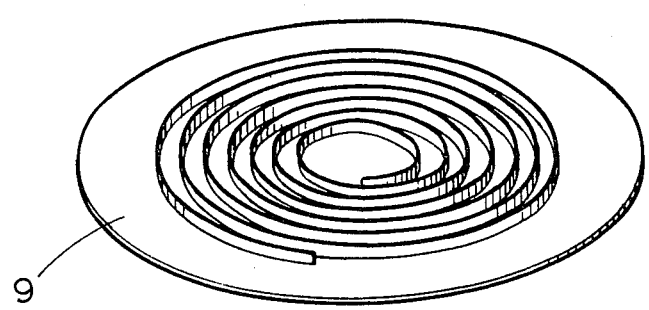
FIG. 4 is a perspective view of a former used in a sealing device.
Figure 5:
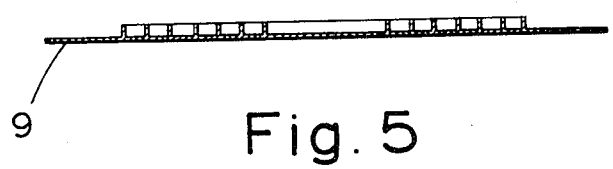
FIG. 5 is a sectional view of the same former.

In the embodiment of the invention illustrated in FIGS. 1 to 3, an ostomy bag is intended to be secured to the body of a patient. The bag is provided by two walls or panels of waterproof plastics material which are sealed together at the edges to provide a bag of the desired shape and with a desired arrangement of openings. For the convenience of description, the wall of the bag which, in use, is brought into contact with the skin of the patient is considered to be the back wall of the bag. The bag has a back wall 1 and a front wall 2. The back wall of the bag has a circular hole which is conveniently in the upper portion of the bag when the bag is in use. This hole is intended to receive the stoma of the patient. The hole is surrounded by a flexible ring or flange 3 the front surface of which is welded to the back surface of the bag by welds 4. The hole in the ring 3 may be smaller than the hole in the back surface of the bag so that the ring reduces the size of the opening in the back wall of the bag or the hole in the ring may be of the same size as that of the opening in the back wall. The rear surface of the ring or flange 3 is adhesive so that the ring or flange can be secured to the body of the patient when the device is in use. The adhesive surface of the ring or flange 3 is covered by release paper 5.

The hole in the back wall of the bag is closed by a disc or sheet of a material capable of adhering to the skin of the patient so as to provide a substantially liquid tight seal. This disc or sheet 6 is provided with cut or slit 8 of generally spiral form. This spiral cut or slit, in effect, defines a closed coil. The disc or sheet preferably has a Karaya gum base. In that case, it is desirable that the slit or cut 8 does not, except possibly as at 8a at the centre of the coil, extend completely through the sheet or disc 6 but penetrates only to a depth of about two thirds to three quarters of the thickness of the sheet. Conveniently, the slit or cut 8 is formed by punching or stamping and the open end of the slit or cut is on the inside of the disc 6. After the slit or cut has been produced in the sheet 6, the adjoining faces of the slit or cut should not re-unite if the sheet has a Karaya gum base. However, if the material of the sheet does tend to re-unite, a chemical barrier agent may be applied to the slit or cut during or immediately after the forming operation to prevent the material re-uniting. If desired, such a chemical barrier agent may be applied to the slit or cut as a spray immediately after the forming operation. The back surface of the disc 6 is covered with a disc 7 of release material. The spiral 8 conveniently, but not essentially has a pitch of two millimeters.

As an alternative to the chemical barrier previously mentioned a pre-formed spiral former 9, conveniently of plastics material may be inserted in the slit or groove 8 after it has been formed to prevent reunion of the material of the sheet 6 at the slit. This former 9 is removed prior to use. If desired, the former may be of a material of sufficient rigidity that the former may be used as a slit-forming punch during the forming operation. In another alternative, a sheet of plastics material may be placed on the sheet prior to the forming operation. The sheet will then be pressed into the slit or cut during the forming operation and remain there after the punch is withdrawn to provide a barrier between the opposite faces of the slit or cut. Where a former is used, it must be accessible from the back of the sheet to permit it to be removed.

In use, the patient removes the release paper and, if one is provided, the former, and pushes out the centre of the sealing sheet or disc. He can then unwind the coil defined by the spiral cut or disc 8 until he produces a hole of a size suitable to fit his stoma. He then cuts off the unwound material and applies the bag to his body, the stoma entering the bag and the area around it being closed in a substantially liquid tight manner by the sealing disc.

What is claimed is:

1. A device for sealing an ostomy bag to the skin of a patient, said device comprising a single sheet of adhesive material capable of adhering to the skin of a patient so as to provide a substantially liquid tight seal, said sheet having a slit extending as a spiral with a portion of said slit near the centre of said spiral extending through the entire thickness of the sheet whereby an aperture of preselected diameter can be produced in the sheet as desired by unwinding a selected length of the coil defined by the spiral slit.

2. A device as claimed in claim 1, wherein said sheet is of a gelatinous material having a basis of Karaya gum.

3. A device as claimed in claim 1, wherein one surface of said sheet is covered by a sheet of release material.

4. A device as claimed in claim 1, wherein a barrier is arranged in said slit to prevent opposed faces of the slit re-uniting.

5. A device as claimed in claim 4, wherein said barrier is a former.

6. A device as claimed in claim 4, wherein said barrier is a chemical barrier.

7. An ostomy bag having a back wall which can be placed in contact with the skin of a patient, the said back wall having a hole in which the stoma of the patient may be received, a flexible ring one surface of which is secured to the back surface of the back wall of the bag and which surrounds the opening in the bag and the other surface of which is adhesive so that it can be secured to the skin of the patient, the hole in the back wall of the bag being closed by a single sheet of adhesive material capable of adhering to the skin of the patient to provide a substantially liquid tight seal, the said sheet being provided with a spiral slit and being secured to the flexible ring, said spiral slit having a portion near the centre thereof extending through the entire thickness of the sheet whereby the spiral can be unwound to form a desired aperature.

* * * * *